United States Patent
Bining et al.

(10) Patent No.: US 11,058,986 B2
(45) Date of Patent: Jul. 13, 2021

(54) MEDICAL GAS PRODUCTION SYSTEM WITH GAS RECYCLING

(71) Applicant: Bining Holdings Ltd., Morden (CA)

(72) Inventors: Gursahib Bining, Morden (CA);
Steven Terichow, Morden (CA)

(73) Assignee: Bining Holdings Ltd., Manitoba (CA)

( * ) Notice: Subject to any disclaimer, the term of this patent is extended or adjusted under 35 U.S.C. 154(b) by 177 days.

(21) Appl. No.: 16/243,579

(22) Filed: Jan. 9, 2019

(65) Prior Publication Data

US 2020/0215478 A1   Jul. 9, 2020

(51) Int. Cl.
*B01D 53/047* (2006.01)
*A61M 16/10* (2006.01)
*B01D 53/053* (2006.01)
*B01D 53/04* (2006.01)
*B01D 53/30* (2006.01)

(52) U.S. Cl.
CPC ....... *B01D 53/0446* (2013.01); *A61M 16/101* (2014.02); *B01D 53/053* (2013.01); *B01D 53/30* (2013.01); *B01D 2253/108* (2013.01); *B01D 2256/12* (2013.01); *B01D 2257/102* (2013.01); *B01D 2259/402* (2013.01); *B01D 2259/40003* (2013.01); *B01D 2259/40009* (2013.01); *B01D 2259/4533* (2013.01)

(58) Field of Classification Search
CPC ............ B01D 53/0446; B01D 53/0476; B01D 53/053; B01D 53/30; B01D 53/108; B01D 2256/12; B01D 2257/102; B01D 2259/40003; B01D 2259/40009; B01D 2259/402; B01D 2259/4533; A61M 16/101; A61M 2016/1025
See application file for complete search history.

(56) References Cited

U.S. PATENT DOCUMENTS

| | | | | |
|---|---|---|---|---|
| 5,346,536 A | * | 9/1994 | Kaneshige | B01D 53/047 95/103 |
| 5,505,765 A | * | 4/1996 | Kaji | B01D 53/053 95/100 |
| 2003/0167924 A1 | * | 9/2003 | McCombs | A61P 11/00 96/121 |
| 2011/0315140 A1 | * | 12/2011 | Shuman | A61M 16/10 128/204.23 |
| 2012/0055475 A1 | * | 3/2012 | Wilkinson | A61M 16/101 128/204.21 |
| 2017/0120085 A1 | * | 5/2017 | Givens | A62B 23/02 |

* cited by examiner

*Primary Examiner* — Jonathan Miller
*Assistant Examiner* — Gabriel E Gitman
(74) *Attorney, Agent, or Firm* — Ryan W. Dupuis; Kyle R. Satterthwaite; Ade & Company Inc.

(57) ABSTRACT

A medical gas production system produces from air a gas composition having a concentration of oxygen greater than the air for subsequent respiration by patients. The system includes a pair of treatment tanks, each containing an adsorbent bed for adsorbing gases from the air and a receiver tank for receiving an oxygen enriched gas mixture from the treatment tanks. A pair of transfer valves connected between receiver tank and respective ones of the treatment tanks control flow of gas from each treatment tank to the receiver tank, as well as enabling backflow of the gas mixture from the receiver tank to the treatment tank if a measured quality of the gas exiting the receiver tank falls below a prescribed threshold.

12 Claims, 3 Drawing Sheets

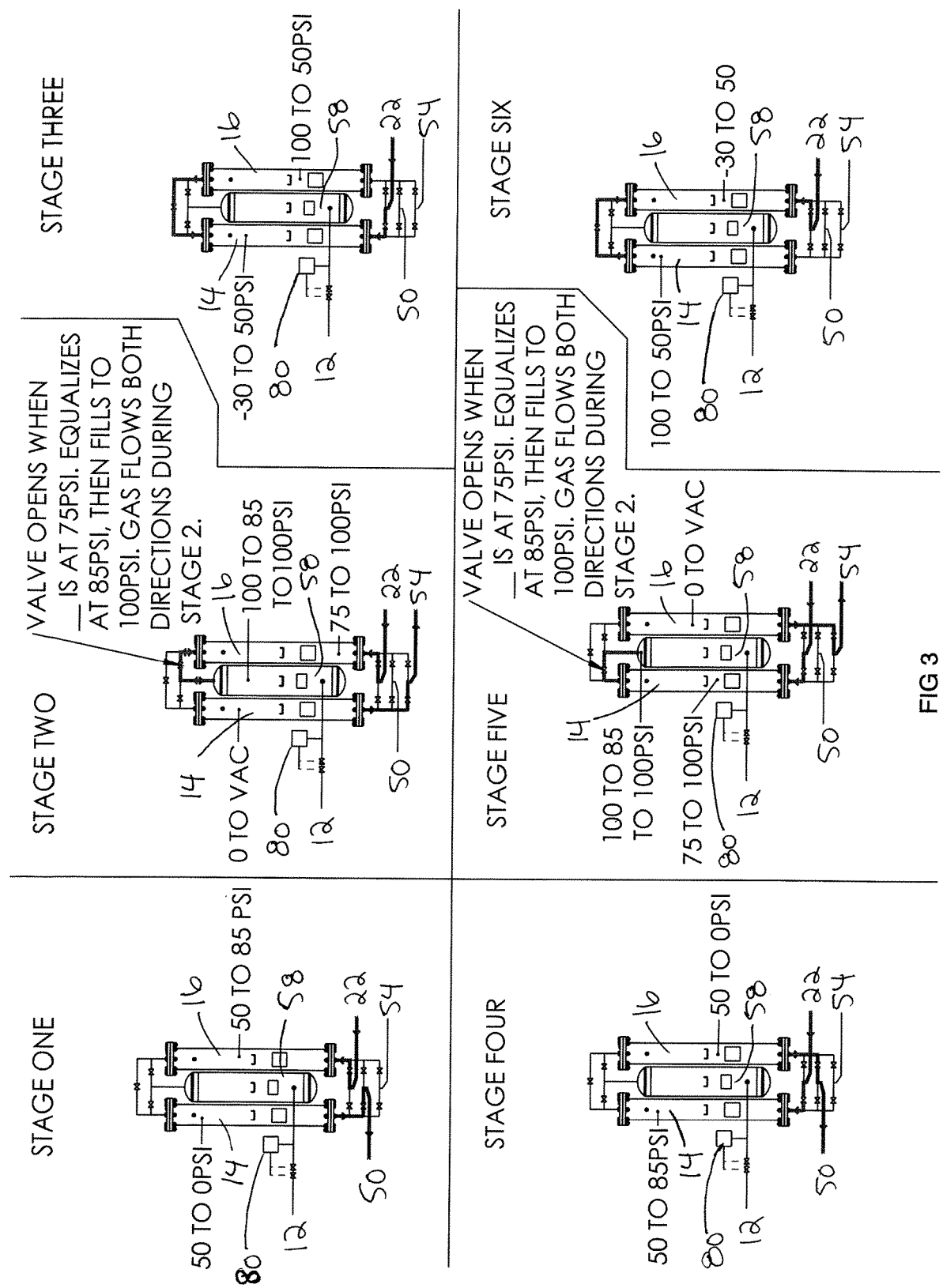

MEDICAL GAS PRODUCTION SYSTEM WITH GAS RECYCLING

FIELD OF THE INVENTION

The present invention relates to a medical gas production system and method of use thereof to produce a gas composition from air in which the gas composition has a concentration of oxygen greater than that of the supplied air so that the oxygen enriched gas composition can be transferred to an external holding tank for subsequent respiration by patients requiring oxygen enriched air for effective breathing.

BACKGROUND

Oxygen concentrators are used in various environments to produce an oxygen enriched gas mixture from atmospheric air that can be used as a medical gas for respiration by patients. A common principle relied upon in many oxygen concentrators is known as pressure swing adsorption (PSA). Wikipedia defines pressure swing adsorption as follows: "Pressure swing adsorption processes utilize the fact that under high pressure, gases tend to be attracted to solid surfaces, or adsorbed. The higher the pressure, the more gas is adsorbed. When the pressure is reduced, the gas is released, or desorbed. PSA processes can be used to separate gases in a mixture because different gases tend to be attracted to different solid surfaces more or less strongly. If a gas mixture such as air is passed under pressure through a vessel containing an adsorbent bed of zeolite that attracts nitrogen more strongly than oxygen, part or all of the nitrogen will stay in the bed, and the gas exiting the vessel will be richer in oxygen than the mixture entering. When the bed reaches the end of its capacity to adsorb nitrogen, it can be regenerated by reducing the pressure, thus releasing the adsorbed nitrogen. It is then ready for another cycle of producing oxygen-enriched air."

A typical oxygen concentrator relies on pressure differential between a series of tanks for moving air to be treated through the tanks. If the quality of the resultant gas mixture is lacking due to an insufficient concentration of oxygen or an undesirable concentration of an impurity, it is known to discharge the treated gas mixture to atmosphere with a new cycle using fresh air from atmosphere being required to produce a replacement treated gas mixture. Discharging to atmosphere is believed to be the most efficient means of preventing usage of a gas mixture of insufficient quality due to the minimal pressure differential which may be available at the final stage of treatment and the desire to avoid additional pumps or compressors to redirect the poor quality gas mixture for further processing. Starting over the production of a treated gas mixture using the same source of air however can result in a continuing quality problem.

SUMMARY OF THE INVENTION

According to one aspect of the invention there is provided a medical gas production system for producing from air a gas composition having a concentration of oxygen greater than the air and delivering the gas composition to an external holding tank for subsequent respiration by patients, the system comprising:

a treatment tank containing an adsorbent bed for adsorbing gases from the air to produce an oxygen concentrated gas mixture;

a receiver tank connected to the treatment tank by at least one transfer line so as to enable transfer of the gas mixture from the treatment tank to the receiver tank;

an outlet line in communication with receiver tank so as to enable transfer of the gas mixture from the receiver tank to the holding tank externally of the system; and at least one transfer valve connected in series with the at least one transfer line between the treatment tank and the receiver tank;

the at least one transfer valve being operable to allow backflow of the gas mixture from the receiver tank to the treatment tank if a measured quality of the gas mixture exiting the receiver tank falls below a prescribed threshold such that further gases may be adsorbed from the gas mixture in a second cycle within the treatment tank.

By enabling some backflow from the receiver tank to the treatment tank, a second stage of absorption is permitted to take place on the same gas mixture to improve the quality thereof such that the resultant quality of the gas mixture is more likely to be improved as compared to starting over the production process with the same initial ambient air. By specifically controlling the timing of the backflow communication from the receiver tank to the treatment tank, very small pressure differentials may be used to drive the backflow without the addition of another pump or compressor being required.

Preferably said at least one transfer line comprises a single line connected between the treatment tank and the receiver tank and said at least one transfer valve comprises a single valve connected in series with the single line so as to be operable between a closed position prevent communication of gases between the treatment tank and the receiver tank and an open position in which gases can be communicated in either one of two opposing directions between the treatment tank and the receiver tank.

The system preferably further comprises: (i) a gas analyser in communication with the outlet line so as to be adapted to measure a characteristic of the gas mixture exiting the receiver tank; and (ii) a controller operatively connected to said at least one transfer valve so as to be adapted to operate the transfer valve automatically to allow backflow of the gas mixture from the receiver tank to the treatment tank if the characteristic of the gas mixture exiting the receiver tank as measured by the gas analyser falls below a prescribed threshold stored on the controller.

The system preferably also further comprises a controller operatively connected to said at least one transfer valve so as to be adapted to operate the valve. In this instance, while the treatment tank is being filled with air and if the measured quality of the gas mixture exiting the receiver tank falls below the prescribed threshold, the controller is preferably adapted to automatically open said at least one transfer valve between the treatment tank and the receiver tank before a pressure within the treatment tank reaches a pressure within the receiver tank such that a pressure differential between the receiver tank and the treatment tank drives the backflow of the gas mixture from the receiver tank to the treatment tank.

The controller may be further adapted to maintain said at least one transfer valve open while the treatment tank is being filled with air until after flow between the treatment tank and the receiver tank reverses and flows from the treatment tank to the receiver tank.

According to a second aspect of the present invention there is provided a A medical gas production system for producing from air a gas composition having a concentration of oxygen greater than the air and delivering the gas composition to an external holding tank for subsequent respiration by patients, the system comprising:

a treatment tank containing an adsorbent bed for adsorbing gases from the air to produce an oxygen concentrated gas mixture;

a receiver tank connected to the treatment tank by at least one transfer line so as to enable transfer of the gas mixture from the treatment tank to the receiver tank;

an outlet line in communication with receiver tank so as to enable transfer of the gas mixture from the receiver tank to the holding tank externally of the system; and at least one transfer valve connected in series with the at least one transfer line between the treatment tank and the receiver tank; and a controller operatively connected to said at least one transfer valve so as to be adapted to operate the valve;

the controller comprising a memory storing programming instructions thereon and a processor adapted to execute the programming instructions such that while the treatment tank is being filled with air, the controller is adapted to automatically open said at least one transfer valve between the treatment tank and the receiver tank before a pressure within the treatment tank reaches a pressure within the receiver tank such that a pressure differential between the receiver tank and the treatment tank drives a backflow of the gas mixture from the receiver tank to the treatment tank.

Preferably the controller is further adapted to maintain said at least one transfer valve open while the treatment tank is being filled with air until after flow between the treatment tank and the receiver tank reverses and flows from the treatment tank to the receiver tank.

According to a further aspect of the present invention there is provided a medical gas production system for producing from air a gas composition having a concentration of oxygen greater than the air and delivering the gas composition to an external holding tank for subsequent respiration by patients, the system comprising:

a receiver tank;

a first treatment tank containing an adsorbent bed for adsorbing gases from the air to produce an oxygen concentrated gas mixture, the first treatment tank being connected to the receiver tank for a first transfer line containing a first transfer valve in series therewith so as to control transfer of gases between the first treatment tank and the receiver tank;

a second treatment tank containing an adsorbent bed for adsorbing gases from the air to produce an oxygen concentrated gas mixture, the second treatment tank being connected to the receiver tank by a second transfer line containing a second transfer valve in series therewith so as to control transfer of gases between the second treatment tank and the receiver tank;

a connecting line in communication between the first treatment tank and the second treatment tank including a connecting valve in series therewith to control transfer of gases between the treatment tank and the second tank;

an outlet line in communication with receiver tank so as to enable transfer of the gas mixture from the receiver tank to the holding tank externally of the system;

a source of compressed air adapted to fill each of the first and second treatment tanks with compressed air independently of one another;

a vacuum source adapted to apply a vacuum pressure to each of the first and second treatment tanks independently of one another; and a controller operatively connected to the valves so as to be adapted to operate the valves;

the controller comprising a memory storing programming instructions thereon and a processor adapted to execute the programming instructions such that the controller is adapted to:

(a) operate the source of compressed air to fill the second treatment tank with compressed air until a pressure within the second treatment tank reaches a prescribed upper pressure value;

(b) operate the vacuum source to reduce a pressure within the first treatment tank until the pressure within the first treatment tank reaches a prescribed vacuum pressure;

(c) while the second treatment tank is being filled with compressed air, (i) open the second transfer valve before the pressure within the second treatment tank reaches the pressure within the receiver tank such that a pressure differential between the receiver tank and the second treatment tank drives a backflow of the gas mixture from the receiver tank to the second treatment tank, and (ii) maintain the second transfer valve open until the gas mixture flows from the second treatment tank to the receiver tank and the pressure in both the receiver tank and the second treatment tank reaches the prescribed upper pressure value;

(d) subsequent to filling the second treatment tank with compressed air, open the connecting valve to transfer some gases from the second treatment tank to the first treatment tank;

(e) operate the source of compressed air to fill the first treatment tank with compressed air until the pressure within the first treatment tank reaches the prescribed upper pressure value;

(f) while the first treatment tank is being filled with air, (i) open the first transfer valve between the first treatment tank and the receiver tank before the pressure within the first treatment tank reaches the pressure within the receiver tank such that a pressure differential between the receiver tank and the first treatment tank drives the backflow of the gas mixture from the receiver tank to the first treatment tank, and (ii) maintain the first transfer valve open until the gas mixture flows from the first treatment tank to the receiver tank and the pressure in both the receiver tank and the first treatment tank reaches the prescribed upper pressure value;

(g) operate the vacuum source to reduce the pressure within the second treatment tank until the pressure within the second treatment tank reaches the prescribed vacuum pressure;

(h) subsequent to filling the first treatment tank with compressed air, open the connecting valve to transfer some gases from the first treatment tank to the second treatment tank; and (i) repeat steps (a) through (h).

BRIEF DESCRIPTION OF THE DRAWINGS

One embodiment of the invention will now be described in conjunction with the accompanying drawings in which:

FIG. 3 illustrates schematic representations of a series of stages of an optimized mode of operation of the system according to FIG. 1.

In the drawings like characters of reference indicate corresponding parts in the different figures.

DETAILED DESCRIPTION

Figure 1:
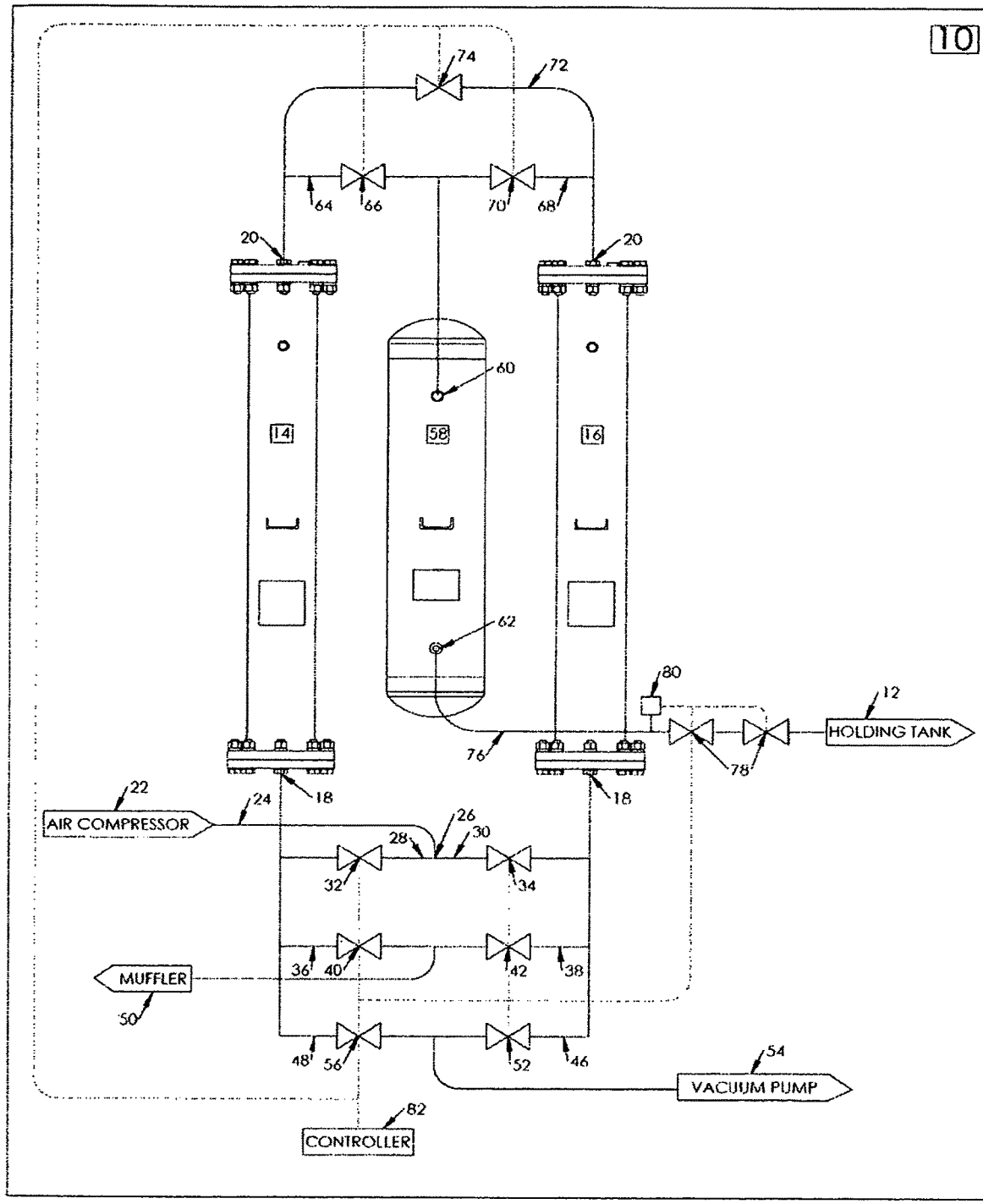
FIG. 1 is a schematic representation of the medical gas production system.

Referring to the accompanying figures, there is illustrated a medical gas production system generally indicated by reference numeral 10. The system 10 is particularly suited for receiving ambient air, typically containing nitrogen, oxygen and other atmospheric gases, for treatment according to a pressure swing adsorption process to produce a resultant gas mixture having a higher concentration of oxygen than the incoming ambient air. The resultant gas mixture produced by the system 10 is delivered to a holding tank 12 which is external of the system. The resultant gas mixture within the external holding tank is a medical gas that is suitable for respiration by patients either alone or combined with ambient air so that the patient breathes the oxygen enriched gas mixture.

The pressure swing adsorption process exposes the gas mixture to be treated under high pressure to an adsorbent bed comprising a molecular sieve such as zeolite. The nitrogen attracts more strongly to the absorbent bed than the oxygen such that part or all of the nitrogen will stay in the bed, and the gas exiting the adsorbent bed will be richer in oxygen than the mixture entering. When the adsorbent bed reaches its capacity to adsorb nitrogen, it can be regenerated by reducing the pressure, thus releasing the adsorbed nitrogen so as to be ready for another cycle of producing oxygen enriched air.

The system 10 according to the illustrated embodiment includes a first treatment tank 14 and a second treatment tank 16, in which each of the treatment tanks contains an adsorbent bed of zeolite therein. When the treatment tanks are filled with pressurized air, the pores of the material in the adsorbent bed are more likely to adsorb nitrogen than oxygen. The gas mixture exiting the treatment tank while under pressure is thus enriched in oxygen relative to the incoming air. After removing the oxygen enriched gas mixture, subsequent depressurization, for example by the application of atmosphere to the treatment tanks, results in the adsorbed gases being desorbed for subsequent expulsion externally from the system 10, for example to vaccum.

Each treatment tank further includes an inlet 18 at the bottom end thereof and an outlet 20 at the top end thereof. Although each inlet primarily receives an incoming flow into the treatment tank and the outlet primarily discharges flow from the outlet tank, both the inlet and the outlet are capable of bidirectional flows into or out of the tank at various stages of the production process as described in further detail below.

The system 10 further includes an air compressor 22 which functions as a supply of compressed air and which communicates with a main supply line 24 which delivers the compressed air to the system. The main supply line 24 is connected to a main tee connector 26 which feeds (i) a first supply line 28 in communication from the main supply line 24 to the inlet of the first treatment tank 14 and (ii) a second supply line 30 in communication from the main supply line 24 to the inlet of the second treatment tank 16.

A first supply valve 32 is connected in series with the first supply line 28 and a second supply valve 34 is connected in series with the second supply line 30. Each of the supply valves is operable between an open condition in which flow of compressed air is permitted from the main supply line 24 into the inlet of the respective treatment tank and a closed position in which communication between the main supply line and the respective treatment tank is interrupted and prevented.

To enable gases to be discharged from the treatment tanks to a location external of the system, for example during the desorbing cycle of the adsorbent bed, a first atmospheric discharge line 36 and a first vacuum discharge line 48 are both in open communication with the first supply line 28 at an intermediate location between the first supply valve and the inlet of the first treatment tank. Similarly, a second atmospheric discharge line 38 and a second vacuum discharge line 46 are both in open communication with the second supply line 30 at an intermediate location between the second supply valve and the inlet of the second treatment tank. A suitable tee connector is provided at the junction of the discharge lines with the respective supply line.

Both of the atmospheric discharge lines 36 and 38 are coupled by a common tee connector to a common discharge vent 50. The discharge vent 50 is equipped with a noise muffler in series therewith which discharges to atmosphere.

To control when gases are discharged through the atmospheric discharge lines 36 and 38 to the discharge vent 50, a first atmospheric discharge valve 40 is provided in series with the first atmospheric discharge line 36 and a second atmospheric discharge valve 42 is provided in series with the second atmospheric discharge line 38. Each of the atmospheric discharge valves is operated between an open condition allowing gases to readily pass through the valve from the respective treatment tank to vent the respective line externally of the system to atmosphere and a closed position in which any discharge flow is prevented through the respective line.

Both of the vacuum discharge lines 48 and 46 are coupled by a common tee connector to a common vacuum line that is connected to a vacuum pump 54. The vacuum pump is operated to provide suction on the vacuum line for selectively applying a vacuum pressure to the treatment tanks through the vacuum discharge lines 48 and 46 when desired.

To control when gases are drawn from the treatment tanks through the vacuum discharge lines 48 and 46 using a vacuum pressure from the vacuum pump, a first vacuum discharge valve 56 is provided in series with the first vacuum discharge line 48 and a second vacuum discharge valve 52 is provided in series with the second vacuum discharge line 46. Each of the vacuum discharge valves is operated between an open condition allowing gases to readily pass through the valve from the respective treatment tank to apply vacuum pressure to expel gasses externally of the system to atmosphere and a closed position in which any discharge flow is prevented through the respective line.

By selectively opening the first atmospheric discharge valve 40, the second atmospheric discharge valve 42, the first vacuum discharge valve 56, and the second vacuum discharge valve 52 independently of one another, either one of the first or second treatment tanks can be discharged to either one of the atmospheric discharge vent 50 or the suction line of the vacuum pump 54 as required by the system for expelling adsorbed gases from the adsorption beds.

During the production process, treated or oxygen-enriched air, that is a gas mixture having a higher concentration of oxygen than the source ambient air, is collected from the outlets of the first and second treatment tanks for subsequent transfer to a receiver tank 58 where the gas mixtures from the two treatment tanks are mixed together prior to discharging to the external holding tank 12. The receiver tank 58 has an inlet 60 at the top end thereof and an outlet 62 at the bottom end thereof. Similarly to the inlet and outlets of the treatment tanks, each of the inlet and outlet of the receiver tank may receive a bi-directional flow therethrough.

A first transfer line 64 is provided in communication from the outlet of the first treatment tank to the inlet of the receiver tank for transferring gases therethrough between the tanks. A first transfer valve 66 is connected in series with the first transfer line so as to be operable between an open position permitting gases to be transferred in either direction from the receiver tank to the first treatment tank, or alternatively from the first treatment tank to the receiver tank, and a closed position in which flow of gases through the first transfer line is prevented.

Similarly, a second transfer line 68 is provided in communication from the outlet of the second treatment tank to the inlet of the receiver tank for transferring gases therethrough between the tanks. A second transfer valve 70 is connected in series with the second transfer line so as to be operable between an open position permitting gases to be transferred in either direction from the receiver tank to the second treatment tank or alternatively from the second treatment tank to the receiver tank, and a closed position in which the flow of gases through the second transfer line is prevented.

A connecting line 72 is also provided which is connected between the outlet of the first transfer tank and the outlet of the second transfer tank. The connecting line is connected to each of the outlets by connection to the first and second transfer lines using respective tee connectors in each of the transfer lines respectively. A connecting valve 74 is connected in series with the connecting line 72 so as to be operable between an open position permitting gases to be transferred in either direction between the two treatment tanks and a closed position in which the flow of gases through the connecting line is prevented.

An outlet line 76 is in communication with the outlet 62 at the bottom of the receiver tank for communicating from the receiver tank to the external holding tank 12. A pair of outlet valves 78 are connected in series with one another within the outlet line 76 such that each outlet valve is able to interrupt flow through the outlet line from the receiver tank to the holding tank. The redundancy of the outlet valves provides added precaution to ensure no flow exits the system.

A gas analyser 80 is in communication with the outlet line at an intermediate location therealong between the outlet of the receiver tank and the external holding tank. The analyser 80 comprises a variety of sensors capable of analysing the contents of the gas mixture flowing through the outlet line. In this manner the analyser is capable of measuring the concentration of oxygen within the gas mixture exiting the receiver tank as well as being capable of measuring the concentration of one or more impurities within the gas mixture such as undesirable gases or toxins for instance.

A suitable controller 82 of the system is provided in the form of a computer in electrical communication with the sensors of the analyser 80 as well as being in communication with each of the valves. All of the valves described herein comprise solenoid actuated valves which can be controlled between open and closed states upon receipt of the appropriate signals from the computer controller 82. The controller 82 further includes a memory storing programming instructions thereon as well as a processor capable of executing the programming instructions to effect the various functions of the system as described in the following.

In a general manner of operation, the various valves of the system are operated to treat a batch of air within each of the treatment tanks in an alternating manner with the resultant oxygen enriched gas being transferred from the treatment tanks to the receiver tank in an alternating manner. The controller typically operates the system in either one of a normal mode or an optimized mode of operation. In the normal mode, a given quantity of gas is treated in a single pass through a respective one of the treatment tanks prior to being transferred to the receiver tank for mixing with other batches of treated gas. In the optimized mode of operation, some gas in the receiver tank is permitted to backflow into one or both of the treatment tanks to undergo a second adsorption cycle to further enrich the oxygen concentration within the gas mixture prior to returning the gas mixture to the receiver tank. The concentration of oxygen within the receiver tank can be increased while simultaneously reducing the concentration of other undesirable gases within the gas mixture in the receiver tank.

The controller typically automatically determines that the system should be operated in the optimized mode if a measurement of the quality of the gas by the analyser is deemed to fall below a prescribed threshold stored on the controller. In one instance, the quality of the gas mixture is determined by the concentration of oxygen such that the quality is below the prescribed threshold if the oxygen concentration falls below a prescribed minimum threshold. Alternatively, the quality of the gas mixture at the outlet of the receiver tank may be considered below threshold quality if the concentration of an impurity or undesirable gas within the gas mixture exceeds a maximum threshold. The controller continues to monitor the quality of the gas mixture in the outlet line or at the outlet of the receiver tank so as to continue to operate in the optimized mode as long as the measured quality remains below the prescribed threshold. Once the measured quality is determined to exceed the prescribed threshold, the controller will then resume operation in the normal mode.

Figure 2:
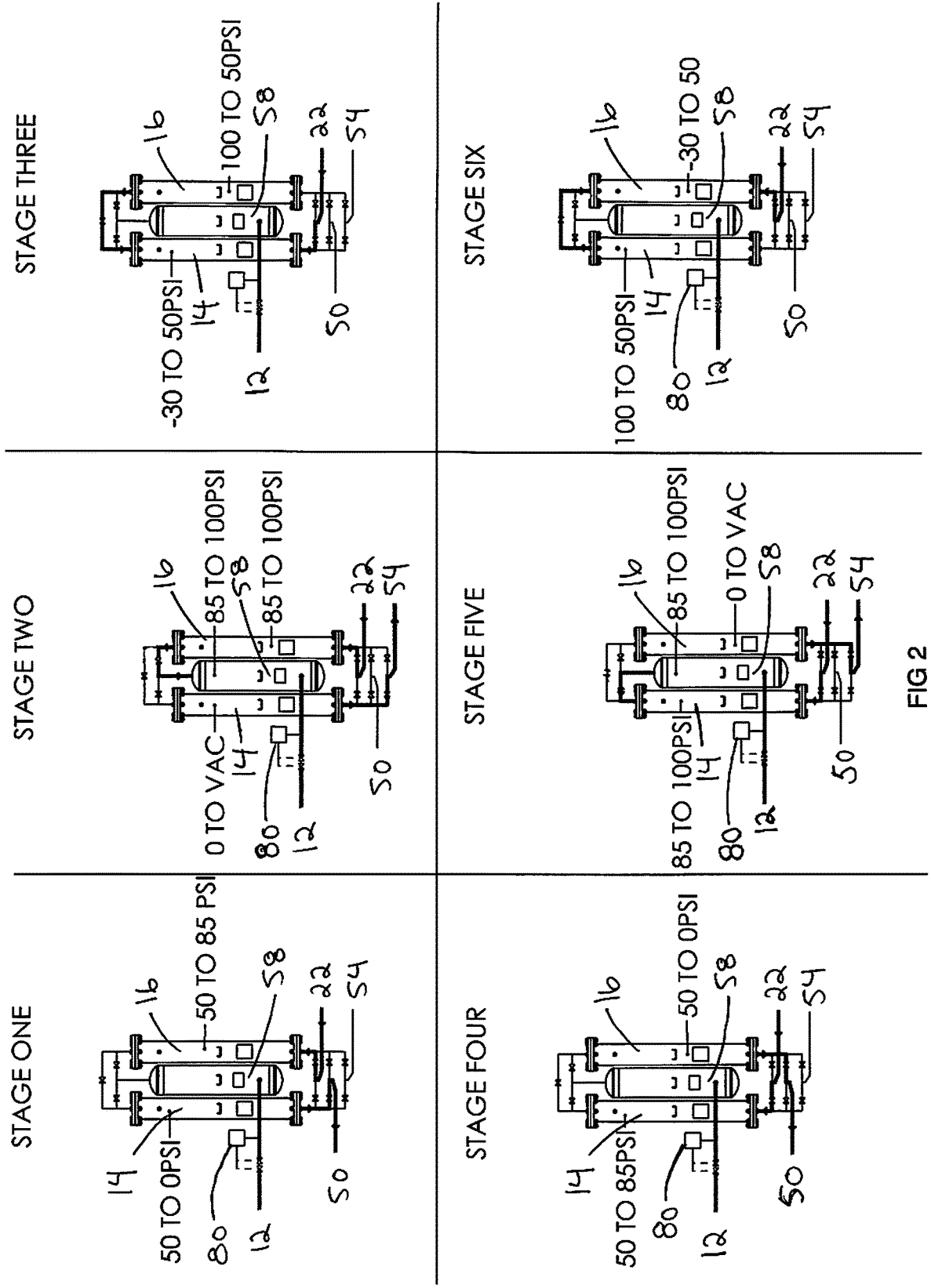
FIG. 2 illustrates schematic representations of a series of stages of a normal mode of operation of the system according to FIG. 1.

Turning now to FIG. 2, the normal mode of operation will now be described in further detail.

In a first stage of the normal mode, the second treatment tank 16 is initially filled using the air compressor to supply compressed air through the second supply line by opening the second supply valve. Simultaneously, the first treatment tank 14 begins undergoing a desorbing cycle by opening the first atmospheric discharge valve 40 for discharging to atmosphere through a suitable muffler. The second treatment tank may be pressurized from 50 to 85 psi for example while the first treatment tank is discharged from 50 to 0 psi for example.

In the second step of the normal mode, the desorbing cycle in the first treatment tank continues by closing the first atmospheric discharge valve 40 and opening the first vacuum discharge valve 56 so that the vacuum pump applies a vacuum pressure to the first treatment tank. Simultaneously, the second treatment tank is continued to be filled with pressurized air from the air compressor. When the pressure within the second treatment tank exceeds a prescribed amount, for example exceeds 85 psi, the second transfer valve is opened such that excess pressure can be communicated from the second treatment tank to the receiver tank 58 by transferring treated gas from the treatment tank to the receiver tank. Compressed air is continued to be pumped into the second treatment tank so that pressure in both the second treatment tank and the receiver tank elevate together to an upper limit, for example 100 psi.

At step three of the normal mode, all of the valves are closed and the connecting valve in the connecting line 72 is opened so that gas can be transferred from the second treatment tank to the first treatment tank which has the effect of reducing pressure in the second treatment tank from an upper limit to a lower limit, for example from 100 down to 50 psi while pressure within the first treatment tank increases from a negative vacuum pressure, for example −30 psi up to 50 psi. The first supply valve remains open so that compressed air can be supplied to the inlet of the first treatment tank to continue to increase the pressure in the first treatment tank.

In step four of the normal mode, the valves are reconfigured for discharging the second treatment tank through the muffler to reduce pressure from 50 psi to zero psi for example while continuing to supply compressed air to the inlet of the first treatment tank to continue to increase the pressure in the first treatment tank, for example from 50 psi to 85 psi. More particularly, the second atmospheric discharge valve 42 is opened for discharging the second treatment tank, while only the first supply valve is opened for pressurizing the first treatment tank from the air compressor.

At step five of the normal mode, the valves are reconfigured so that the second vacuum discharge valve 52 is opened for continuing the desorbing cycle of the second treatment tank by applying a vacuum pressure to the second treatment tank, while the first supply valve remains open to continue pressurizing the first treatment tank. When pressure within the first treatment tank exceeds a prescribed amount, for example exceeds 85 psi, the first transfer valve is opened such that the excess pressure can be communicated from the first treatment tank to the receiver tank 58 by transferring treated gas from the treatment tank to the receiver tank. Compressed air is continued to be pumped into the first treatment tank so that pressure in both the first treatment tank and the receiver tank elevate together to an upper limit for example 100 psi.

At step six of the normal mode, the controller reconfigures the valves again similarly to step three in which the connecting line 72 is opened so that gas can be transferred from the first treatment tank to the second treatment tank which has the effect of reducing pressure in the first treatment tank from an upper limit to a lower limit, for example from 100 down to 50 psi, while pressure within the second treatment tank increases from a negative vacuum pressure, for example −30 psi up to 50 psi. The second supply valve remains opened so that compressed air can be supplied to the inlet of the second treatment tank to continue to increase the pressure in the second treatment tank.

The process of the normal mode then resumes back to step one to follow through the various steps once again by continuing to pressurize the second treatment tank up to an upper limit, for example from 50 psi to 85 psi, while the first treatment tank again undergoes the beginning of a desorbing cycle by opening the first atmospheric discharge valve 40 for discharging to atmosphere.

Turning now to FIG. 3, the optimized mode of operation will now be described in further detail.

In the first step of the optimized mode, the valves are controlled similarly to the normal process such that the second treatment tank 16 is initially filled using the air compressor to supply compressed air through the second supply line by opening the second supply valve. Simultaneously, the first treatment tank 14 begins undergoing a desorbing cycle by opening the first atmospheric discharge valve 40 for discharging to atmosphere through a suitable muffler. The second treatment tank may be pressurized from 50 to 85 psi for example while the first treatment tank is discharged from 50 to 0 psi for example.

In the second step of the optimized mode, the desorbing cycle in the first treatment tank continues by closing the first atmospheric discharge valve 40 and opening the first vacuum discharge valve 56 so that the vacuum pump applies a vacuum pressure to the first treatment tank. Simultaneously, the second treatment tank is continued to be filled with pressurized air from the air compressor. When the pressure within the second treatment tank exceeds an intermediate pressure level which is less than the pressure of the receiver tank 58, the second transfer valve is opened. For example, the second transfer valve can be opened when the pressure in the receiver tank 58 is at 80 psi but the pressure in the second treatment tank is only at 75 psi such that a previously treated gas mixture within the receiver tank 58 backflows through the second transfer line into the second treatment tank until the receiver tank and the second treatment tank stabilize at a balanced pressure, for example at 77 psi. Throughout this process, the air compressor can remain activated with the second supply valve being opened to supply compressed air through the second supply line into the second treatment tank. The second transfer valve 70 remains open such that pressure within both the second treatment tank and the receiver tank elevate together from 77 psi up to 100 psi with gases from the second treatment tank continuing to flow from the second treatment tank into the receiver tank through this later part of the second stage of the optimized process.

At step three of the optimized mode, the second transfer valve 70 that was open in step two initially remains open while the connecting valve 74 in the connecting line 72 is opened. The second transfer valve remains open until the receiver tank drops to approximately 80 psi as some of the gas in the receiver tank flows back through the transfer valve and subsequently through the connecting line 72 into the first treatment tank 14. The connecting valve 74 remains open subsequent to closing of the second transfer valve 70 so that gas is continued to be transferred from the second treatment tank to the first treatment tank which has the effect of reducing pressure in the second treatment tank from an upper limit to a lower limit, for example from 100 down to 50 psi while pressure within the first treatment tank increases from a negative vacuum pressure, for example −30 psi up to 50 psi. The first supply valve 32 also remains opened throughout step three so that compressed air can be supplied to the inlet of the first treatment tank to continue to increase the pressure in the first treatment tank.

In step four of the optimized mode, the valves are reconfigured for discharging the second treatment tank through the muffler of the discharge line to reduce pressure from 50 psi to zero psi for example while continuing to supply compressed air to the inlet of the first treatment tank to continue to increase the pressure in the first treatment tank, for example from 50 psi to 75 psi. More particularly, only the second atmospheric discharge valve 42 is opened for discharging the second treatment tank, while only the first supply valve 32 is opened for pressurizing the first treatment tank from the air compressor.

In step five of the optimized mode, the process is similar to step two of the optimized process but with flow of gases being exchanged between the first treatment tank and the receiver tank instead of between the second treatment tank and the receiver tank according to step two. More particularly, in step five of the optimized mode, the desorbing cycle in the second treatment tank continues by closing the second atmospheric discharge valve 42 and opening the second vacuum discharge valve 52 so that the vacuum pump applies a vacuum pressure to the second treatment tank. Simultaneously the first treatment tank is continued to be filled with pressurized air from the air compressor. When the pressure within the first treatment tank exceeds an intermediate pressure level which is less than the pressure of the receiver tank 58, the first transfer valve is opened. For example, the first transfer valve can be opened when the pressure in the receiver tank is at 80 psi but the pressure in the first treatment tank is only at 75 psi such that a previously treated gas mixture within the receiver tank 58 backflows through the first transfer line into the first treatment tank until the receiver tank and the first treatment tank stabilize at a balanced pressure, for example at 77 psi. Throughout this process, the air compressor can remain activated with the first supply valve being opened to supply compressed air through the first supply line into the first treatment tank. The first transfer valve_66 remains open such that the pressure within both the first treatment tank and the receiver tank elevate together from 77 psi up to 100 psi with gases from the first treatment tank continuing to flow from the first treatment tank into the receiver tank through this later part of the fifth stage of the optimized process.

At step six of the optimized mode, the first transfer valve 66 that was open in step five initially remains open while the connecting valve 74 in the connecting line 72 is opened. The first transfer valve 66 remains open until the receiver tank drops to approximately 80 psi as some of the gas in the received receiver tank flows back through the transfer valve and subsequently through the connecting line 72 into the second treatment tank 16. The connecting valve 74 remains open subsequent to closing the first transfer valve 66 so that gas is continued to be transferred from the first treatment tank to the second treatment tank which has the effect of reducing pressure in the first treatment tank from an upper limit to a lower limit, for example from 100 down to 50 psi, while pressure within the second treatment tank increases from a negative vacuum pressure, for example −30 psi up to 50 psi. The second supply valve 34 remains opened throughout step five so that compressed air can be supplied to the inlet of the second treatment tank to continue to increase the pressure in the second treatment tank.

As described herein, in the normal cycle the treatment tanks fill the receiver tank. This one-way flow will keep the receiver tank full and it will feed the external holding tank.

In the optimized cycle the timing of the valving will open the transfer valve to the receiver tank early and the receiver tank will drain some of the stored pressure into the treatment tank that is pressurizing to get filtered twice and by keeping the transfer valve open it will fill back into the receiver tank. The valve between the receiver tank and the pressurizing treatment tank will open when the treatment tank is at 75 psi. Due to the discharge valves being closed the receiver tank pressure is about 80 psi when the receiver tank valve opens to the pressurizing treatment tank. About 5 psi of the receiver tank will dump into the treatment tank. They will typically equalize at about 77 psi. The valve stays open and the treatment tank and the receiver tank will fill to 100 psi. The same process is repeated every treatment tank fill where 5 psi of the receiver tank gets re-filtered by the pressurizing treatment tank. By leaving the transfer valve open for additional time, about 20 psi of gas in the receiver tank will be transferred to the pressurizing treatment tank, dropping the pressure in the receiver tank to 80 psi and then refilling the pressure back to 100 psi by the same treatment tank.

By recycling some of the gas from receiver tank back into one or both treatment tanks for a second cycle of treatment within the adsorbent bed, the quality of the gas is improved. The analyzers will monitor the quality and when the quality of the gas is confirmed to be OK, the optimized cycle is over and the gas will flow from the receiver tank to the external holding tank. The flow then proceeds only in a direction from the treatment tanks to the receiver tank since the quality in the receiver tank does not need to be filtered twice.

The opening and closing of the various valves is determined by the controller using a controller which measures a duration of each step in the process and reconfigures the valves to the next step configuration upon expiration of the prescribed duration for that step. The prescribed duration of each step to cause the tanks to be filled and discharged at the prescribed pressures noted above is determined during initial calibration of the system for a given configuration of tanks and connection lines having prescribed volumes and flow transfer rates. Once the prescribed duration for each step is determined during initial calibration of a prescribed system configuration, the same durations can be used by controllers of all other systems with the same system configuration of tanks and flow lines.

In alternative embodiments, pressure sensors may be operatively conntected to each of the tanks for measuring the pressure in the tank and communicating the pressure back to the controller as a sensor signal so that the valves can be opened and closed when the measured pressure reaches the desired pressure value instead of operating the valves at each step according to a prescribed duration associated with each step that is stored on the controller. The use of pressure sensors increases the cost and complexity of the system and is typically not required if using a system configuration of tank sizes and flow lines which has been calibrated to determine the prescribed duration for each step of the normal and optimized processes noted above.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. A medical gas production system for producing from air a gas composition having a concentration of oxygen greater than the air and delivering the gas composition to an external holding tank for subsequent respiration by patients, the system comprising:

a treatment tank containing an adsorbent bed for adsorbing gases from the air to produce an oxygen concentrated gas mixture;

a receiver tank connected to the treatment tank by at least one transfer line so as to enable transfer of the gas mixture from the treatment tank to the receiver tank;

an outlet line in communication with the receiver tank so as to enable transfer of the gas mixture from the receiver tank to the external holding tank;

at least one transfer valve connected in series with the at least one transfer line between the treatment tank and the receiver tank; and a controller operatively connected to said at least one transfer valve so as to be adapted to operate the at least one transfer valve;

the controller comprising a memory storing programming instructions thereon and a processor adapted to execute the programming instructions such that the controller is adapted to automatically open said at least one transfer valve between the treatment tank and the receiver tank (i) while the treatment tank is being filled with air from a source other than the receiver tank and (ii) before a pressure within the treatment tank reaches a pressure within the receiver tank such that a pressure differential between the receiver tank and the treatment tank drives a backflow of the gas mixture from the receiver tank to the treatment tank.

2. The system according to claim 1, wherein the controller is further adapted to maintain said at least one transfer valve open while the treatment tank is being filled with air from said source other than the receiver tank until after flow between the treatment tank and the receiver tank reverses and flows from the treatment tank to the receiver tank.

3. The system according to claim 1, wherein the controller is adapted to operate said at least one transfer valve to allow said backflow only if a measured quality of the gas mixture exiting the receiver tank falls below a prescribed threshold.

4. The system according to claim 3, further comprising a gas analyser in communication with the outlet line so as to be adapted to measure said measured quality of the gas mixture and communicate said measured quality to the controller.

5. The system according to claim 1, wherein said at least one transfer line comprises a single line connected between the treatment tank and the receiver tank and wherein said at least one transfer valve comprises a single valve connected in series with the single line so as to be operable between a closed position to prevent communication of gases between the treatment tank and the receiver tank and an open position in which gases can be communicated in either one of two opposing directions between the treatment tank and the receiver tank.

6. A medical gas production system for producing from air a gas composition having a concentration of oxygen greater than the air and delivering the gas composition to an external holding tank for subsequent respiration by patients, the system comprising:
   a receiver tank;
   a first treatment tank containing an adsorbent bed for adsorbing gases from the air to produce an oxygen concentrated gas mixture, the first treatment tank being connected to the receiver tank few by a first transfer line containing a first transfer valve in series therewith so as to control transfer of gases between the first treatment tank and the receiver tank;
   a second treatment tank containing an adsorbent bed for adsorbing gases from the air to produce an oxygen concentrated gas mixture, the second treatment tank being connected to the receiver tank by a second transfer line containing a second transfer valve in series therewith so as to control transfer of gases between the second treatment tank and the receiver tank;
   a connecting tine in communication between the first treatment tank and the second treatment tank including a connecting valve in series therewith to control transfer of gases between the first treatment tank and the second treatment tank;
   an outlet line in communication with the receiver tank so as to enable transfer of the gas mixture from the receiver tank to the external holding tank;
   a source of compressed air adapted to fill each of the first and second treatment tanks with compressed air independently of one another;
   a vacuum source adapted to apply a vacuum pressure to each of the first and second treatment tanks independently of one another; and
   a controller operatively connected to the valves so as to be adapted to operate the valves;

the controller comprising a memory storing programming instructions thereon and a processor adapted to execute the programming instructions such that the controller is adapted to:
   (a) operate the source of compressed air to fill the second treatment tank with compressed air until a pressure within the second treatment tank reaches a prescribed upper pressure value;
   (b) operate the vacuum source to reduce a pressure within the first treatment tank until the pressure within the first treatment tank reaches a prescribed vacuum pressure;
   (c) while the second treatment tank is being filled with compressed air from said source, (i) open the second transfer valve before the pressure within the second treatment tank reaches the pressure within the receiver tank such that a pressure differential between the receiver tank and the second treatment tank drives a backflow of the gas mixture from the receiver tank to the second treatment tank, and (ii) maintain the second transfer valve open until the gas mixture flows from the second treatment tank to the receiver tank and the pressure in both the receiver tank and the second treatment tank reaches the prescribed upper pressure value;
   (d) subsequent to filling the second treatment tank with compressed air, open the connecting valve to transfer some gases from the second treatment tank to the first treatment tank;
   (e) operate the source of compressed air to fill the first treatment tank with compressed air until the pressure within the first treatment tank reaches the prescribed upper pressure value;
   (f) while the first treatment tank is being filled with air from said source, (i) open the first transfer valve between the first treatment tank and the receiver tank before the pressure within the first treatment tank reaches the pressure within the receiver tank such that a pressure differential between the receiver tank and the first treatment tank drives the backflow of the gas mixture from the receiver tank to the first treatment tank, and (ii) maintain the first transfer valve open until the gas mixture flows from the first treatment tank to the receiver tank and the pressure in both the receiver tank and the first treatment tank reaches the prescribed upper pressure value;
   (g) operate the vacuum source to reduce the pressure within the second treatment tank until the pressure within the second treatment tank reaches the prescribed vacuum pressure;
   (h) subsequent to filling the first treatment tank with compressed air, open the connecting valve to transfer some gases from the first treatment tank to the second treatment tank; and
   (i) repeat steps (a) through (h).

7. The system according to claim 6, wherein the controller is adapted to operate said first transfer valve and said second transfer valve to allow said backflow only if a measured quality of the gas mixture exiting the receiver tank falls below a prescribed threshold.

8. The system according to claim 7, further comprising a gas analyser in communication with the outlet line so as to be adapted to measure said measured quality of the gas mixture and communicate said measured quality to the controller.

9. The system according to claim 7, wherein the controller is adapted to operate said at least one transfer valve to allow said backflow only if a measured quality of the gas mixture exiting the receiver tank falls below a prescribed threshold.

10. The system according to claim 9, further comprising a gas analyser in communication with the outlet line so as to be adapted to measure said measured quality of the gas mixture and communicate said measured quality to the controller.

11. The system according to claim 10, wherein said at least one transfer line comprises a single line connected between the treatment tank and the receiver tank and wherein said at least one transfer valve comprises a single valve connected in series with the single line so as to be operable between a closed position to prevent communication of gases between the treatment tank and the receiver tank and an open position in which gases can be communicated in either one of two opposing directions between the treatment tank and the receiver tank.

12. A medical gas production system for producing from air a gas composition having a concentration of oxygen greater than the air and delivering the gas composition to an external holding tank for subsequent respiration by patients, the system comprising:
   a treatment tank containing an adsorbent bed for adsorbing gases from the air to produce an oxygen concentrated gas mixture;
   a receiver tank connected to the treatment tank by at least one transfer line so as to enable transfer of the gas mixture from the treatment tank to the receiver tank;
   an outlet line in communication with the receiver tank so as to enable transfer of the gas mixture from the receiver tank to the external holding tank;
   at least one transfer valve connected in series with the at least one transfer line between the treatment tank and the receiver tank;
   a source of compressed air adapted to fill the treatment tank through a supply line including a supply valve in series with the supply line between the source of compressed air and the treatment tank;
   a vacuum source adapted to apply a vacuum pressure to the treatment tank through a vacuum line including a vacuum valve in series with the vacuum line between the vacuum source and the treatment tank; and
   a controller operatively connected to said at least one transfer valve, the supply valve, and the vacuum valve so as to be adapted to operate the valves;
   the controller comprising a memory storing programming instructions thereon and a processor adapted to execute the programming instructions such that the controller is adapted to:
   (i) reduce pressure within the treatment tank until pressure within the treatment tank reaches a prescribed vacuum pressure by opening the vacuum valve;
   (ii) fill the treatment tank with compressed air until the pressure within the treatment tank reaches a prescribed upper pressure value by opening the supply valve;
   (iii) subsequent to the treatment tank being partly filled so that the pressure in the treatment tank is greater than the prescribed vacuum pressure and less than the prescribed upper pressure value, operate said at least one transfer valve between the treatment tank and the receiver tank in an open state while the pressure within the treatment tank is less than a pressure within the receiver tank such that a pressure differential between the receiver tank and the treatment tank drives a backflow of some of the gas mixture from the receiver tank to the treatment tank; and
   (iv) subsequent to said backflow of some of the gas mixture from the receiver tank to the treatment tank, operate said at least one transfer valve in an open state while the pressure in the treatment tank exceeds the pressure in the receiver tank such that some of the gas mixture flows from the treatment tank to the receiver tank before the pressure in the treatment tank reaches the prescribed upper pressure value.

* * * * *